United States Patent
Patriciu et al.

(10) Patent No.: US 12,004,825 B2
(45) Date of Patent: Jun. 11, 2024

(54) MULTI-STAGE ROBOT FOR ANATOMICAL STRUCTURE INTERVENTIONS

(71) Applicant: KONINKLIJKE PHILIPS N.V., Eindhoven (NL)

(72) Inventors: Alexandru Patriciu, Belmont, MA (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 420 days.

(21) Appl. No.: 16/762,660

(22) PCT Filed: Nov. 6, 2018

(86) PCT No.: PCT/EP2018/080297
§ 371 (c)(1),
(2) Date: May 8, 2020

(87) PCT Pub. No.: WO2019/091962
PCT Pub. Date: May 16, 2019

(65) Prior Publication Data
US 2021/0177530 A1    Jun. 17, 2021

Related U.S. Application Data

(60) Provisional application No. 62/585,254, filed on Nov. 13, 2017.

(51) Int. Cl.
*A61B 34/30* (2016.01)
*A61B 17/00* (2006.01)
(Continued)

(52) U.S. Cl.
CPC ........ *A61B 34/30* (2016.02); *A61B 17/00234* (2013.01); *A61B 2017/0034* (2013.01);
(Continued)

(58) Field of Classification Search
CPC .............. A61B 34/30; A61B 17/00234; A61B 2017/0034; A61B 2034/2055;
(Continued)

(56) References Cited

U.S. PATENT DOCUMENTS 8,573,226 B2    11/2013    Saadat et al.
8,620,473 B2 *  12/2013    Diolaiti .............. A61B 1/00087
                                                        600/407
(Continued)

FOREIGN PATENT DOCUMENTS

JP    2008502421 A    1/2008
WO       05046461     5/2005
WO     2013080124     6/2013

OTHER PUBLICATIONS

International Search Report and Written Opinion dated Feb. 26, 2019 for International Application No. PCT/EP2018/080297 Filed Nov. 6, 2018, see pp. 1-7.
(Continued)

*Primary Examiner* — Sarah W Aleman
*Assistant Examiner* — Mikail A Mannan (57) ABSTRACT

A multi-stage robot (10) comprises a sequential series arrangement of a flexible robot arm (30), a robot platform (40), a snake robot arm (50) and an end-effector (60). In operation, the multi-state robot (10) is introduced through an incision or an anatomical opening into an anatomical region enclosing an anatomical structure, and the snake robot arm (50) and the end-effector (60) are further introduced through an incision or an anatomical opening into the anatomical structure. The robot platform (40) is thereafter attached to the incision or the anatomical opening of the anatomical structure to facilitate an actuation of the snake robot arm (50) relative to the robot platform (40) to thereby target position the end-effector (60) within the anatomical structure. The multi-stage robot (10) may further comprise a
(Continued)

robot base at the proximal end of the multi-stage robot (10) and attachable to the incision or the anatomical opening into the anatomical region.

18 Claims, 4 Drawing Sheets

(51) Int. Cl.
*A61B 34/20* (2016.01)
*A61B 90/00* (2016.01)
*A61F 2/24* (2006.01)

(52) U.S. Cl.
CPC .............. *A61B 2034/2055* (2016.02); *A61B 2034/2061* (2016.02); *A61B 2034/301* (2016.02); *A61B 2034/302* (2016.02); *A61B 2090/3782* (2016.02); *A61B 2090/3983* (2016.02); *A61F 2/2427* (2013.01)

(58) Field of Classification Search
CPC ...... A61B 2034/2061; A61B 2034/301; A61B 2034/302; A61B 2090/3782; A61B 2090/3983; A61B 2017/00783; A61B 2034/2051; A61B 2034/2063; A61B 2090/374; A61B 34/72; A61B 90/37; A61B 2017/00243; A61B 2017/00247; A61B 2018/00351; A61B 2018/00369; A61B 2034/304; A61B 2034/305; A61B 2090/376; A61B 2090/378; A61F 2/2427
See application file for complete search history.

(56) References Cited

U.S. PATENT DOCUMENTS

| | | |
|---|---|---|
| 2005/0029978 A1 | 2/2005 | Oleynikov |
| 2009/0123111 A1 | 5/2009 | Udd |
| 2014/0058406 A1 | 2/2014 | Tsekos |
| 2015/0119900 A1* | 4/2015 | Simaan .............. A61B 1/00006 606/130 |
| 2016/0144510 A1 | 5/2016 | Gulhar |
| 2018/0014891 A1* | 1/2018 | Krebs .................... A61B 17/15 |
| 2018/0263711 A1 | 9/2018 | Popovic |
| 2018/0370045 A1* | 12/2018 | Kan ....................... A61B 34/71 |
| 2019/0069955 A1 | 3/2019 | Popovic |

OTHER PUBLICATIONS

Light, et al: "Progress in Ring Array Transducers for Real-Time 3D Ultrasound Guidance of Cardiac Interventional Devices" Ultrason Imaging. Jul. 2011; 33(3): 197-204.

Light, et al: "New fabrication techniques for ring-array transducers for real-time 3D intravascular ultrasound," Ultrason Imaging. Oct. 2009;31(4):247-56.

Guerra, et al: "Robot-integrated intraoperative ultrasound: Initial experience with hepatic malignancies", Minimally Invasive Therapy, 2015, 345-349.

* cited by examiner

MULTI-STAGE ROBOT FOR ANATOMICAL STRUCTURE INTERVENTIONS

CROSS REFERENCE TO RELATED APPLICATIONS

This application is the U.S. National Phase application under 35 U.S.C. § 371 of International Application No. PCT/EP2018/080297 filed Nov. 6, 2018, published as WO 2019/091962 on May 16, 2019, which claims the benefit of U.S. Provisional Patent Application No. 62/585,254 filed Nov. 13, 2017. These applications are hereby incorporated by reference herein.

FIELD OF THE INVENTION

The present disclosure generally relates to robots for performing various interventional procedures (e.g., aortic valve displacements and mitral valve repairs). The present disclosure specifically relates to a multi-stage robot attachable to a wall of an anatomical structure (e.g., a heart, a stomach, an intestine and a bladder) for facilitating a target positioning of an end-effector within the anatomical structure.

BACKGROUND OF THE INVENTION

In minimally invasive structural heart disease interventions, the surgeons deploy valves or other devices that correct heart pathologies using X-ray and/or ultrasound guidance. The access to the deployment site is either trans-catheter or trans-apical and the deployment accuracy is very important for the procedure's success. For example, if an aortic valve is placed too "high", then the aortic valve may obstruct the coronary arteries. By further example, when a mitral clip used to correct mitral valve regurgitation is deployed, the surgeon has to ensure that the clip catches properly the mitral valve leaflets in order for it to be effective. The challenges of these procedures is to obtain a full imagery of the anatomy and/or to acquire full three-dimensional ("3D") information and physiological motion of the anatomy (the anatomy is moving with the heart beat and the respiratory cycle).

The current minimally invasive approach to treat structural heart diseases relies on manual guidance using fluoroscopy and ultrasound feedback. However, the delineation of the anatomy in such image modalities is hard to identify and is subject to physiological motion of the anatomy. Additionally, a position of the therapy delivery device with respect to the anatomy has to be inferred in real time by the surgeon from available images, and there is no automatic registration of the therapy device to the anatomy or imaging dataset. Furthermore, positioning of the therapy device may be challenging as the conventional approach is to use catheters in a trans-catheter approach or straight sheath in a trans-apical approach.

More particularly, in an aortic valve replacement using a trans-apical approach, the surgeon uses a straight sheath for valve delivery. During the intervention, the surgeon has to align the chest incision with the apex of the heart and with the aortic valve. This may be challenging and if repositioning is required, this may apply a stress on the heart's apex.

Using a small slender robot that has sensing at the end-effector has proven to provide positioning accuracy and feedback that is required in such procedures. The sensors on the end-effector will allow for the automatic registration of the robot with respect to the anatomy segmented from preoperative or intraoperative imaging of the robot. Additionally, the robot will allow for automatic adjustment of the device position with respect to the anatomy of interest. These two features allow for more accurate treatment delivery and faster procedures.

SUMMARY OF THE INVENTION

As an improvement to robots for interventional procedures on anatomical structures (e.g., a heart, a stomach, an intestine and a bladder), the present disclosure describes a multi-stage robot including a non-actuatable positioning stage and an actuatable positioning stage whereby a junction of the two (2) stages is attachable to an incision into the anatomical structure for facilitating a target positioning of an end-effector within the anatomical structure.

One embodiment of the inventions of the present disclosure is a multi-stage robot for a target positioning of an intervention tool within an anatomical structure (e.g., a heart). The multi-stage robot comprises a sequential series arrangement of a flexible robot arm, a robot platform, an snake robot arm and an end-effector. In operation, the flexible robot arm, the robot platform, the snake robot arm and the end-effector are introduced through an incision or an anatomical opening into an anatomical region enclosing an anatomical structure (e.g., an incision into a thoracic pericardial cavity enclosing a heart), and the snake robot arm and the end-effector are further introduced through an incision into the anatomical structure (e.g., an incision into the heart). The robot platform is thereafter attached to the incision or the anatomical opening of the anatomical structure to facilitate an actuation of the snake robot arm relative to the robot platform to thereby target position the end-effector within the anatomical structure.

A second embodiment of the inventions of the present disclosure is the multi-stage robot further comprising a robot base at the proximal end of the multi-stage robot and attachable to the incision or the anatomical opening into the anatomical region.

For purposes of describing and claiming the inventions of the present disclosure:

(1) terms of the art of the present disclosure are to be interpreted as known in the art of the present disclosure and exemplary described and/or further defined in the present disclosure. Examples of the terms of the present disclosure include, but not limited to, interventional procedure, intervention tool, anatomical region, anatomical structure, anatomical opening, incision, markers, shape sensors, motion sensors, distance sensors and end-effector;

(2) the term "interventional procedure" broadly encompasses all interventional procedures, as known in the art of the present disclosure or hereinafter conceived, for an imaging, a diagnosis and/or a treatment of a patient anatomy;

(3) the term "intervention space" broadly encompasses a coordinate space enclosing the interventional procedure as exemplary described in the present disclosure;

(4) the term "intervention tool" broadly encompasses, as understood in the art of the present disclosure and hereinafter conceived, a tool, an instrument, a device or the like for conducting an imaging, a diagnosis and/or a treatment of a patient anatomy. Examples of intervention tools include, but are not limited to, scalpels, cauterizers, ablation devices, balloons, stents, endografts, atherectomy devices, clips, needles, forceps, and endoscopes;

(5) the term "sequential series arrangement" broadly encompasses an sequential arrangement of components in a series extending from a proximal end of multi-stage robot to a distal end of multi-stage robot as exemplary described herein. Examples of a sequential series arrangement of the present disclosure include (proximal end) flexible robot arm-robot platform-snake robot arm-end-effector (distal end), and (proximal end) robot base-flexible robot arm-robot platform-snake robot arm-end-effector (distal end);

(6) the term "robot base" broadly encompasses all intervention accessories or intervention devices, as known in the art of the present disclosure and hereinafter conceived, structured for establishing a proximal point of origin for the multi-stage robot. Examples of robot bases include, but are not limited to, a general purpose positioning robot, a passive positioning arm and a fixture;

(7) the term "flexible robot arm" broadly encompasses all flexible cylindrical medical devices utilized in interventional procedures as known in the art of the present disclosure and hereinafter conceived. Examples of flexible robot arms include, but are not limited to, a catheter and passive snake-like robots;

(8) the term "robot platform" broadly encompasses all intervention accessories or intervention devices, as known in the art of the present disclosure and hereinafter conceived, structured for attachment to an incision into an anatomical structure. Examples of robot bases include, but are not limited to, a cuff of a flexible robot arm and clips mounted on the flexible robot;

(9) the term "snake robot arm" broadly encompasses all robotic arms, as known in the art of the present disclosure and hereinafter conceived, structured for actuating a translation, a rotation, and/or pivoting of an end-effector relative to a robot platform. Examples of snake robot arms include, but are not limited to, serial articulated robot arms structures similar with the ones employed by the da Vinci® Robotic System, the Medrobotics Flex® Robotic System, the Magellan™ Robotic System, and the CorePath® Robotic System;

(10) the term "end-effector" broadly encompasses all accessory devices, as known in the art of the present disclosure and hereinafter conceived, for attachment to a snake robot arm for facilitating a performance of a task by the multi-stage robot in support of an intervention procedure within an anatomical structure;

(11) the term "target position" broadly encompasses a position for an end-effector within an anatomical structure that facilitates a delivery of an interventional tool by the end-effector within the anatomical structure.

(12) the term "target positioning" broadly encompasses all techniques, as known in the art of the present disclosure and hereinafter conceived, for actuating a snake robot arm to position the end-effector at the target position within the anatomical structure. Examples of such techniques include, but are not limited to, image-based guidance of a snake robot arm, image based feedback position control, and image based real time target tracking;

(13) the term "adjoined" and any tense thereof broadly encompasses a detachable or a permanent coupling, connection, affixation, clamping, mounting, etc. of components;

(14) the term "controller" broadly encompasses all structural configurations, as understood in the art of the present disclosure and as exemplary described in the present disclosure, of an application specific main board or an application specific integrated circuit for controlling an application of various inventive principles of the present disclosure as subsequently described in the present disclosure. The structural configuration of the controller may include, but is not limited to, processor(s), computer-usable/computer readable storage medium(s), an operating system, application module(s), peripheral device controller(s), slot(s) and port(s). A controller may be housed within or linked to a workstation. Examples of a "workstation" include, but are not limited to, an assembly of one or more computing devices, a display/monitor, and one or more input devices (e.g., a keyboard, joysticks and mouse) in the form of a standalone computing system, a client computer of a server system, a desktop or a tablet;

(15) the descriptive labels for term "controller" herein facilitates a distinction between controllers as described and claimed herein without specifying or implying any additional limitation to the term "controller";

(16) the term "application module" broadly encompasses an application incorporated within or accessible by a controller consisting of an electronic circuit and/or an executable program (e.g., executable software stored on non-transitory computer readable medium(s) and/or firmware) for executing a specific application;

(17) the terms "signal", "data" and "command" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Signal/data/command communication between components of a coaxial robotic system of the present disclosure may involve any communication method as known in the art of the present disclosure including, but not limited to, signal/data/command transmission/reception over any type of wired or wireless datalink and a reading of signal/data/commands uploaded to a computer-usable/computer readable storage medium; and (18) the descriptive labels for terms "signal", "data" and "commands" herein facilitates a distinction between signals/data/commands as described and claimed herein without specifying or implying any additional limitation to the terms "signal", "data" and "command".

The foregoing embodiments and other embodiments of the inventions of the present disclosure as well as various features and advantages of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of present disclosure being defined by the appended claims and equivalents thereof.

DETAILED DESCRIPTION OF THE PREFERRED EMBODIMENTS

Figure 1:
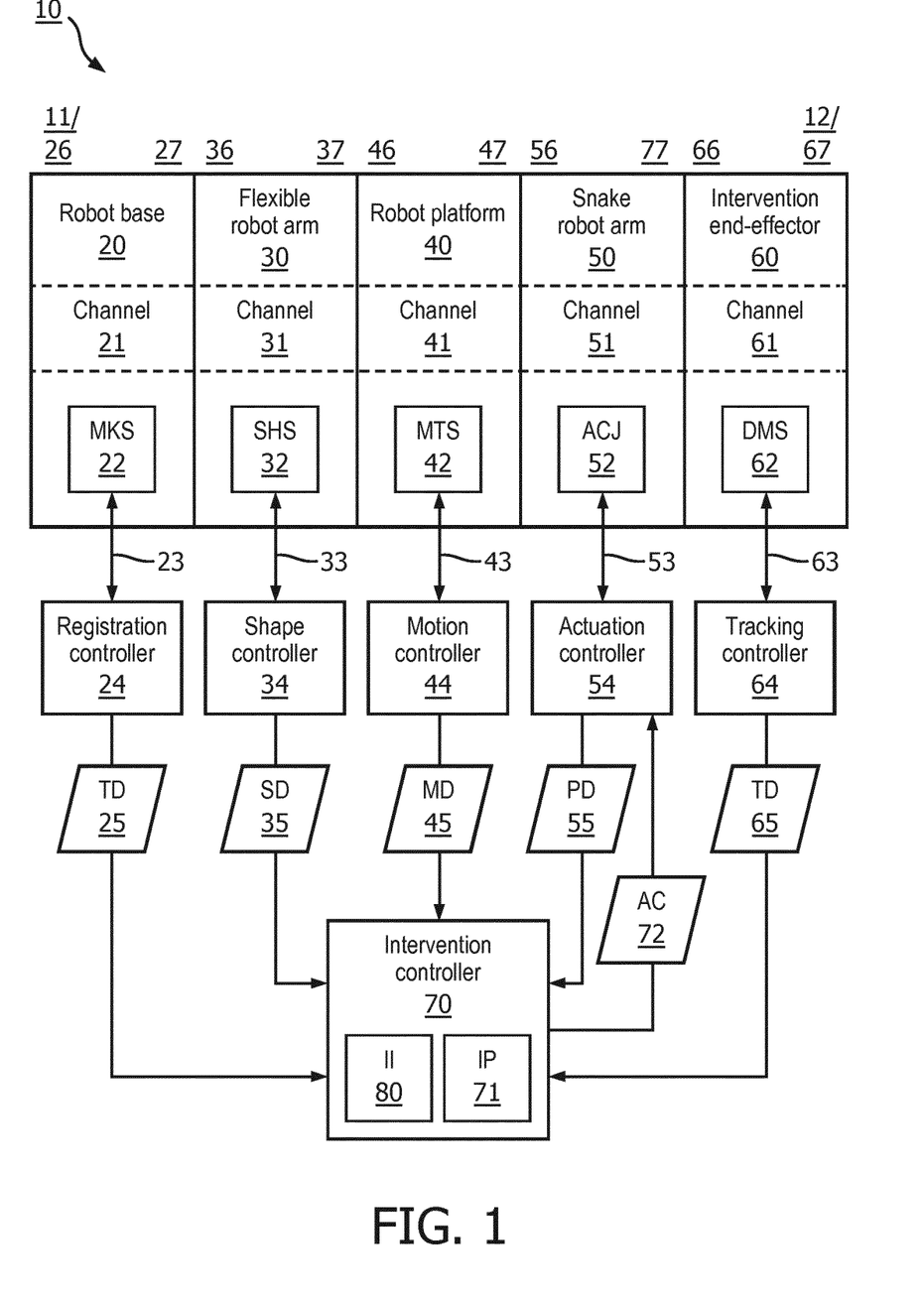
FIG. 1 illustrates exemplary embodiments of a multi-stage robot and a control network in accordance with the inventive principles of the present disclosure.
Figure 2:
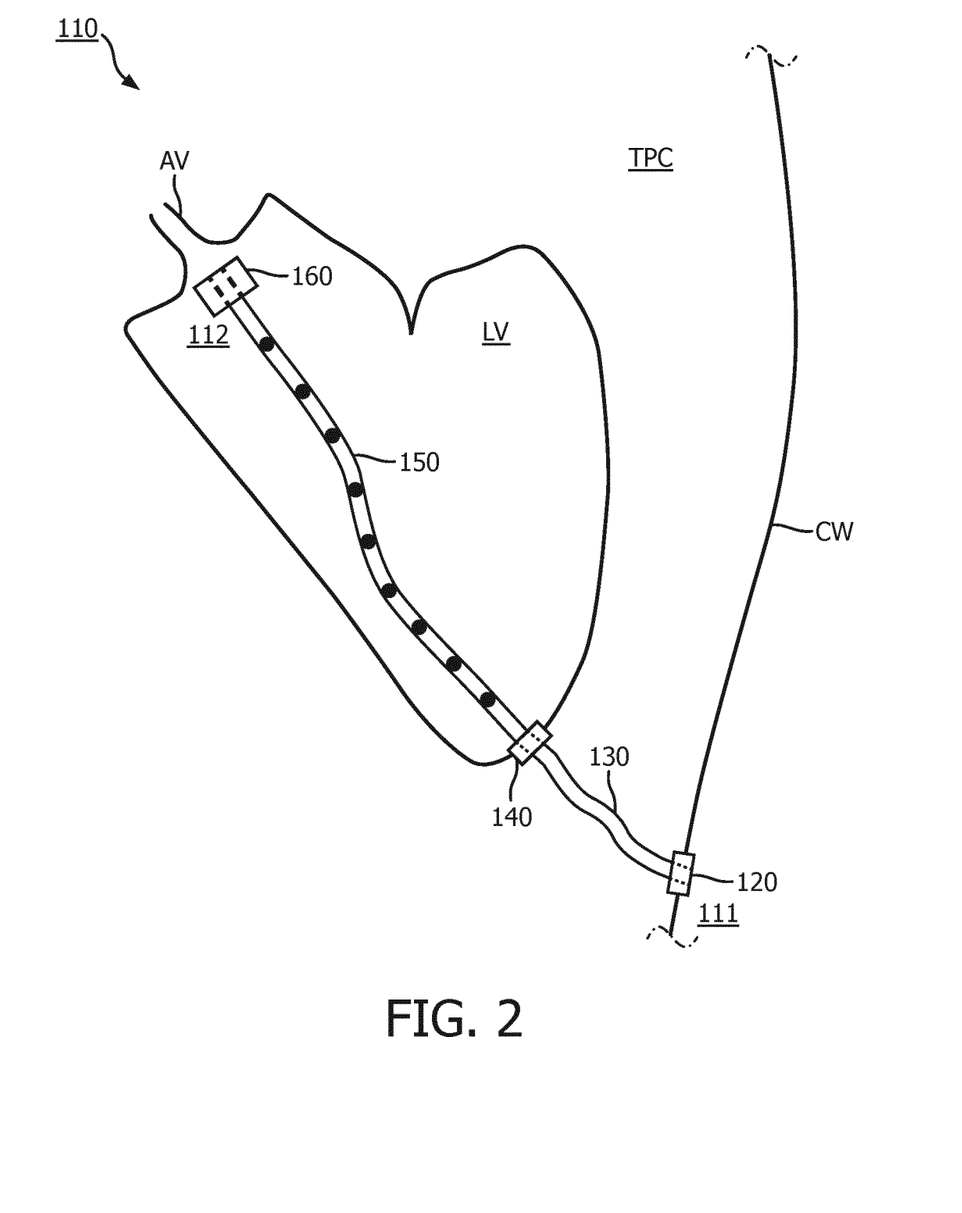
FIG. 2 illustrates an exemplary embodiment of the multi-stage robot of FIG. 1 in accordance with the inventive principles of the present disclosure.

To facilitate an understanding of the inventions of the present disclosure, the following description of FIGS. 1 and 2 teaches basic inventive principles of exemplary embodiments of a multi-stage robot and a control network of the present disclosure. From this description, those having ordinary skill in the art will appreciate how to apply the inventive principles of the present disclosure to making and using numerous and varied embodiments of a multi-stage robot and control network of the present disclosure.

Referring to FIG. 1, a multi-stage robot 10 of the present disclosure employs a robot base 20, a flexible robot arm 30, a robot platform 40, a snake robot arm 50 and an end-effector 60 for performing an interventional procedure involving an imaging, a diagnosis and/or treatment of an anatomical structure (e.g., a heart, a lung, a stomach, an intestine and a bladder) via a target positioning of end-effector 60 within the anatomical structure.

Robot base 20 implements a robot position tracking stage of robot 10 involving robot base 20 serving as a point of origin for a position tracking of robot 10 relative to an imaging modality to thereby facilitate a visualization of end-effector 60 within interventional images of the anatomical structure generated by the imaging modality and/or facilitate an autonomous control by an intervention controller 70 of the target positioning of end-effector 60 within the anatomical structure.

In practice, robot base 20 may have a fixed position or a variable position within an intervention space of the interventional procedure.

In one embodiment, robot base 20 is affixed to or fixedly positioned relative to the imaging modality within the intervention space as will be further exemplary described in the present disclosure.

In a second embodiment, robot base 20 is structured to be attachable to an incision or an anatomical opening into an anatomical region (i.e., a thoracic region, a cranial region, an abdominal region, etc.) enclosing the anatomical structure as will be further exemplary described in the present disclosure. For example, robot base 20 may be attached to an incision into a thoracic pericardial cavity enclosing a heart, an incision into a thoracic pleural cavity enclosing lungs, an incision into an abdominopelvic abdominal cavity enclosing a stomach or an incision into an abdominopelvic pelvic cavity enclosing a bladder.

Further in practice, robot base 20 may have a channel 21 for delivery of an intervention tool to end-effector 60 as will be further exemplary described in the present disclosure.

Further in practice, robot base 20 may include one or more markers 22 to facilitate an identification of the fixed position or the variable position of robot base 20 within the intervention space. For example, robot base 20 may include marker 22 in the form of an optical marker identifiable within the intervention space by an optical tracker as known in the art of the present disclosure. By further example, robot base 20 may include marker 22 in the form of a fluoroscopic marker identifiable within the intervention space by a fluoroscopic imaging modality as known in the art of the present disclosure.

Further in practice, robot base 20 may be omitted from robot 10 whereby any reference within the intervention space may serve as an origin for position tracking robot 10.

Still referring to FIG. 1, robot platform 40 implements an end-effector target positioning stage of robot 10 involving robot platform 40 serving as a point of origin for a target positioning of end-effector 60 within the anatomical structure to thereby further facilitate a visualization of end-effector 60 within interventional images of the anatomical structure generated by an imaging modality and/or facilitate an autonomous control by intervention controller 70 of the target positioning of end-effector 60 within the anatomical structure.

In practice, robot platform 40 represents a junction between flexible robot arm 30 and snake robot arm 50 and is structured to be attachable to an incision or an anatomical opening into the anatomical structure, whereby flexible robot arm 30 is positioned within the anatomical region external to the anatomical structure and snake robot arm 50 is positioned within the anatomical structure as will be further exemplary described in the present disclosure.

Further in practice, robot platform 40 may have a channel 41 for delivery of an intervention tool to end-effector 60 as will be further exemplary described in the present disclosure.

Further in practice, robot platform 40 may include one or more motion sensors 42 to facilitate a detection of any physiological motion of the anatomical structure. For example, robot platform 40 may include motion sensors 42 in the form of accelerometers for a detection of any physiological motion of the anatomical structure as known in the art of the present disclosure.

Still referring to FIG. 1, flexible robot arm 30 implements a non-actuatable positioning stage of robot 10 involving a portion or an entirety of flexible robot arm 30 within the anatomical region extending from an incision or an anatomical opening into the anatomical region to an incision into the anatomical structure.

In practice, flexible robot arm 30 is structured for facilitating the attachment of robot platform 40 to the incision into the anatomical structure and has a material composition for following any physiological motion of the anatomical structure as will be further exemplary described in the present disclosure.

Further in practice, flexible robot arm 30 may have a channel 31 for delivery of an intervention tool to end-effector 60 as will be further exemplary described in the present disclosure.

Further in practice, flexible robot arm 30 includes one or more shape sensors 32 for tracking a shape of flexible robot arm 30 that is representative of a distance between robot base 20 and robot platform 40, particularly in view of any physiological motion of the anatomical structure. For example, flexible robot arm 30 includes one or more shape sensors 32 in the form of optical shape sensor(s) for tracking a shape of flexible robot arm 30 as known in the art of the present disclosure.

In one embodiment, flexible robot arm 30 is an optical shape sensing catheter as will be further exemplary described in the present disclosure.

Still referring to FIG. 1, snake robot arm 50 implements an actuatable positioning stage of robot 10 involving an actuation of snake robot arm 50 for target positioning end-effector 60 within the anatomical structure for delivery of an intervention tool within the anatomical structure.

In practice, snake robot arm 50 may be any type of snake robot arm as known in the art of the present disclosure.

In one embodiment, snake robot arm 50 includes a proximal linkage, a distal linkage and optionally including one or more intermediate linkages. Snake robot arm 50 further includes actuator joint(s) 52 interconnecting the linkages in a serial arrangement. Examples of an actuator joint include, but are not limited to, a translational actuator joint, a ball and socket actuator joint, a hinge actuator joint, a condyloid actuator joint, a saddle actuator joint and a rotary actuator joint.

Further in practice, snake robot arm 50 may have a channel 51 for delivery of an intervention tool to end-effector 60 as will be further exemplary described in the present disclosure.

Further in practice, actuator joints 52 of snake robot arm 50 may be actuatable by any technique known in the art of the present disclosure.

In one embodiment, each actuator joint 52 is actuatable by an actuation controller 54 via actuation signals for controlling a location and orientation of each linkage relative to robot platform 40, and each actuator joint 52 includes a pose sensor of any type (e.g., an encoder) for generating a pose signal informative of the location and orientation of each linkage relative to a robot platform 40.

In a second embodiment, each actuator joint 52 is tendon driven by an operator of robot 10 for controlling an actuation of each linkage, and each actuator joint 52 again includes a pose sensor of any type (e.g., an encoder) for generating a pose signal informative of the location and orientation of each linkage relative to a robot platform 40.

Still referring to FIG. 1, end-effector 60 implements a tool delivery stage of robot 10 involving a delivery of an intervention tool from a target location of end-effector within the anatomical structure to conduct an imaging, a diagnosis and/or a treatment of the anatomical structure in accordance with an interventional procedure as known in the art of the present disclosure.

In practice, end-effector 60 has a structural form suitable for delivery of one or more particular intervention tools to the target location within the anatomical structure.

In one embodiment, end-effector 60 may have a channel 61 for directing the intervention tool within the anatomical structure as known in the art of the present disclosure. For this embodiment, end-effector 60 may be actuatable to translate, rotate and/or pivot channel 61 relative to a distal end of snake robot arm 50 as known in the art of the present disclosure.

In a second embodiment, end-effector 60 may have the intervention tool detachably supported by end-effector 60. For this embodiment, end-effector 60 again may be actuatable to translate, rotate and/or pivot channel 61 relative to a distal end of snake robot arm 50 as known in the art of the present disclosure.

Further in practice, end-effector 60 may include one or more distance sensors 62 for measuring distance(s) of end-effector 60 from one or more walls of the anatomical structure to thereby further facilitate a target positioning of end-effector 60 within the anatomical structure.

In one embodiment, end-effector 60 includes a distance sensor 62 in the form of a ring ultrasound array for generating a "looking forward" ultrasound image of an interior of the anatomical structure as known in the art of the present disclosure whereby the ultrasound image generated by the ring ultrasound array facilitates the target positioning of end-effector 60 within the anatomical structure and further may be fused with an image of the anatomical structure segmented from pre-operative and/or intraoperative interventional images as known in the art of the present disclosure.

In a second embodiment, end-effector 60 includes distance device 62 in the form of a set of one-dimensional forward looking ultrasound probes for generating an image line emanating from end-effector 60 whereby the image line generated by the ultrasound probes also facilitates the target positioning of end-effector 60 within the anatomical structure and further may also be fused with the image of the anatomical structure segmented from pre-operative and/or intraoperative interventional images as known in the art of the present disclosure. More particularly, a dense ultrasound image of the interior of the anatomical structure may be formed from multiple generated image lines as end-effector 60 is moved within the anatomical structure.

Still referring to FIG. 1, multi-stage robot 10 has a sequential serial arrangement of components 20, 30, 40 and 50 with (1) robot base 20 being adjoined to a proximal end of flexible robot arm 30, (2) end-effector 60 being adjoined to a distal end of snake robot arm 50, and (3) robot platform 40 being adjoined to a distal end of flexible robot arm 30 and/or a proximal end of snake robot arm 50. With this serial arrangement of components 20, 30, 40 and 50, if applicable, channels 21, 31, 41 and 51 are axially aligned, preferably co-axially aligned, to form a robot channel extending from a proximal end 11 of robot 10 towards a distal end 12 of robot 10 whereby an intervention tool may be extended through the robot channel to end-effector 60.

In practice, components 20, 30, 40 and 50 of robot 10 may be adjoined in any manner suitable for introducing the robot 10 into the anatomical structure and for implementing each stage of robot 10 as previously described in the present disclosure.

In one embodiment, a distal end 27 of robot base 20 is detachably coupled or permanently affixed to a proximal end 36 of flexible robot arm 30.

In a second embodiment, proximal end 36 of flexible robot arm 30 extends into or through channel 21 of robot base 20, which is clamped to or integrated with flexible robot arm 30.

In a third embodiment, a proximal end of robot platform 40 is detachably connected or permanently affixed to a distal end 37 of flexible robot arm 30 and a distal end 47 of robot platform 40 is detachably connected or permanently affixed to a proximal end 56 of snake robot arm 50 to thereby couple proximal end 37 of flexible robot arm 30 to a distal end 56 of snake robot arm 50.

In a fourth embodiment, distal end 37 of flexible robot arm 30 extends into or through channel 41 of robot platform 40, which is clamped to or integrated with flexible robot arm 30, and distal end 37 of flexible robot arm 30 is further detachably connected or permanently affixed to proximal end 56 of snake robot 50.

In a fifth embodiment, proximal end 56 of snake robot arm 50 extends into or through channel 41 of robot platform 40, which is clamped to or integrated with snake robot arm 50, and distal end 37 of flexible robot arm 30 further detachably connected or permanently affixed to proximal end 56 of snake robot 50.

In a sixth embodiment, distal end 37 of flexible robot arm 30 is further detachably connected or permanently affixed to proximal end 56 of snake robot 50 within channel 41 of robot platform 40, which is clamped to the flexible robot arm 30 and the snake robot arm 50.

End-effector 60 is adjoined to snake robot arm 50 in a manner suitable for delivery of the intervention tool as known in the art of the present disclosure.

Still referring to FIG. 1, a control network for robot 10 includes a shape controller 34, actuation controller 54 and intervention controller 70, and may further include a registration controller 24 (applicable if robot base 20 incorporates marker(s) 22), a motion controller 44 (applicable if robot platform 40 incorporates motion sensor(s) 42) and a tracking controller 64 (applicable if end-effector 60 incorporates distance sensor(s) 62).

If applicable, an interaction 23 between marker(s) 22 and registration controller 24 is established via a tracking machine (e.g., an optical tracker or an electromagnetic tracker) whereby registration controller 24 controls an operation of the tracking machine for implementing one or more registration techniques as known in the art of the present disclosure involving an identification of marker(s) 22 within the intervention space and a generation by registration controller 24 of registration data 25 informative of a positioning of robot base 20 relative to the imaging modality (e.g., X-ray machine).

For example, as previously described, optical markers may be affixed to robot base 20 and the imaging modality whereby registration controller 24 controls an operation of an optical tracker having registration controller 24 installed therein or linked thereto to thereby identify the optical markers within the intervention space and generate the registration data 25.

An interaction 33 between shape sensor(s) 32 and shape controller 34 is established via a shape sensing machine (i.e., an optical integrator for optical shape sensor(s)) and shape controller 34 controls an operation of the shape sensing machine as installed therein or linked thereto for implementing one or more shape sensing techniques as known in the art of the present disclosure involving a determination of a shape of flexible robot arm 30.

For example, for embodiments having shape sensor(s) 32 in the form of optical shape sensor(s) (e.g., optical fiber(s) including Fiber Bragg gratings or a Raleigh scattering), shape controller 34 controls an optical integrator supplying light to the optical shape sensors to thereby determine a shape of flexible robot arm 30 via light transmitted through or reflected back from the optical shape sensors. For this example, the optical shape sensor is integrated into the flexible robot arm 30 as known in the art and extends through or along robot base 20 to the optical integrator, which is connected to a workstation having intervention controller 70 installed therein.

If applicable, a wired connection 43 is established between motion sensor(s) and motion controller 44 whereby motion controller 44 receives signals from motion sensor(s) 42 informative of any physiological motion of the incision into the anatomical structure. For this embodiment, the wired connection 43 extends from robot platform 40 sequentially through or along flexible robot arm 30 and robot base 20 to a workstation having motion controller 44 installed therein.

A wired connection 53 is established between actuated joints 52 and actuation controller 54 whereby actuation controller 54 receives pose signals informative of a pose (i.e., orientation and/or location) of each linkage of snake robot arm 50 relative to robot platform 40 as known in the art of the present disclosure and generates pose data 55 from the pose signals. Additionally, actuation controller 54 may control an operation of actuated joints 52 via wired connection 53. For this embodiment, the wired connection 53 extends from snake robot arm 50 sequentially through or along robot platform 40, flexible robot arm 30 and robot base 20 to a workstation having actuation controller 54 installed therein.

If applicable, an interface 63 between distance devices 62 and tracking controller 64 is established via an ultrasound machine whereby tracking controller 64 controls an operation of distance sensors 62 via the ultrasound machine to thereby generate tracking data 65 informative of a position of end-effector 60 within the interior of the anatomical structure. For example, as previously discussed, distance sensor(s) 62 may in the form of a ring ultrasound array or a set of 1D ultrasound probes whereby tracking controller 64 energies the ultrasound elements via the ultrasound machine to thereby generate tracking data 65 in the form of ultrasound images. For this embodiment, the wired connection 63 extends from end-effector 60 sequentially through or along snake robot arm 50, robot platform 40, flexible robot arm 30 and robot base 20 to a workstation having tracking controller 64 installed therein.

Intervention controller 70 implements the interventional procedure by controlling a display of preoperative and/or interoperative intervention images 80 (e.g., X-ray, CT, MRI, etc.) of the anatomical structure in accordance with a preoperative plan for a target positioning end-effector 60 within the anatomical structure as known in the art of the present disclosure, which may include a fusion of any generated ultrasound image of the interior of the anatomical structure.

In one embodiment, intervention controller 70 displays a position of end-effector 60 within intervention images 80 of the anatomical structure as indicated from all of the data.

In a second embodiment, intervention controller generates an overlay of end-effector 60 (and a portion or an entirety of snake robot arm 50) onto intervention images 80 as indicated from all of the data.

Intervention controller 70 may further control an actuation of snake robot arm 50 as known in the art of present disclosure via actuation commands 72 derived from a conformance or any deviation in accordance with a preoperative plan of a target positioning on end-effector 60 within the anatomical structure as indicated by all the data.

In practice, all of the controllers of FIG. 1 may be installed on a same workstation, or distributed in any manner among a plurality of workstations.

Further in practice, all of the controllers of FIG. 1 may be segregated as shown, or two (2) or more of the controllers may be fully or partially integrated.

To further understand multi-stage robot 10, FIG. 2 illustrates an embodiment 110 of robot 10 as introduced into a left ventricle chamber LV of a heart to perform an aortic valve replacement of aortic valve AV.

Referring to FIG. 2, robot 110 includes a robot base 120, a flexible robot arm 130 in the form of an optical shape sensing catheter, a robot platform 140, a snake robot arm 150 and an end-effector 160.

Robot base 120 is a proximal cuff of flexible robot arm 130 and is attached to an incision of a chest wall CW of a thoracic pericardial cavity TPC via a suture. Alternatively, robot base 120 may be a launch device for the optical shape sensing catheter that is affixed externally to the thoracic pericardial cavity TPC to a reference point in the intervention space whereby flexible robot arm extends into the entry of the chest wall CW of the thoracic pericardial cavity TPC.

Robot platform 130 is a distal cuff of flexible robot arm 130 and is attached to an incision into the left ventricle chamber LV of the heart via a suture.

Flexible robot arm 130 flexibly extends within the thoracic pericardial cavity between robot base 120 and robot platform 140.

Snake robot arm 150 is adjoined to robot platform 130 and extends into the left ventricle chamber LV of the heart.

End-effector 160 is adjoined to snake robot arm 150 and actuatable to be translated and/or pivoted relative to snake robot arm 150.

A position of end-effector 160 within the left ventricle chamber LV of the heart is derived from (1) a registration of robot base 120 to a corresponding imaging modality, (2) a sensed shape of flexible robot arm 130, (3) a sensed physiological motion of the left ventricle chamber LV (if applicable), (4) a pose of each linkage of snake robot arm 150 relative to robot platform 140, and (5) an ultrasound imaging of the interior of the left ventricle chamber LV (if applicable).

As such, snake robot arm 150 may be actuated, manually or via intervention controller 70 (FIG. 1), as needed for a target positioning of end-effector 160 relative to the aortic valve AV via a preoperative plan to thereby deliver the valve replacement via a balloon as known in the art of the present disclosure.

In practice, robot base 120 may be omitted whereby flexible robot arm 130 is sutured to the incision into the chest wall CW of the thoracic pericardial cavity and proximally extends to a reference within the intervention space.

Figure 3:
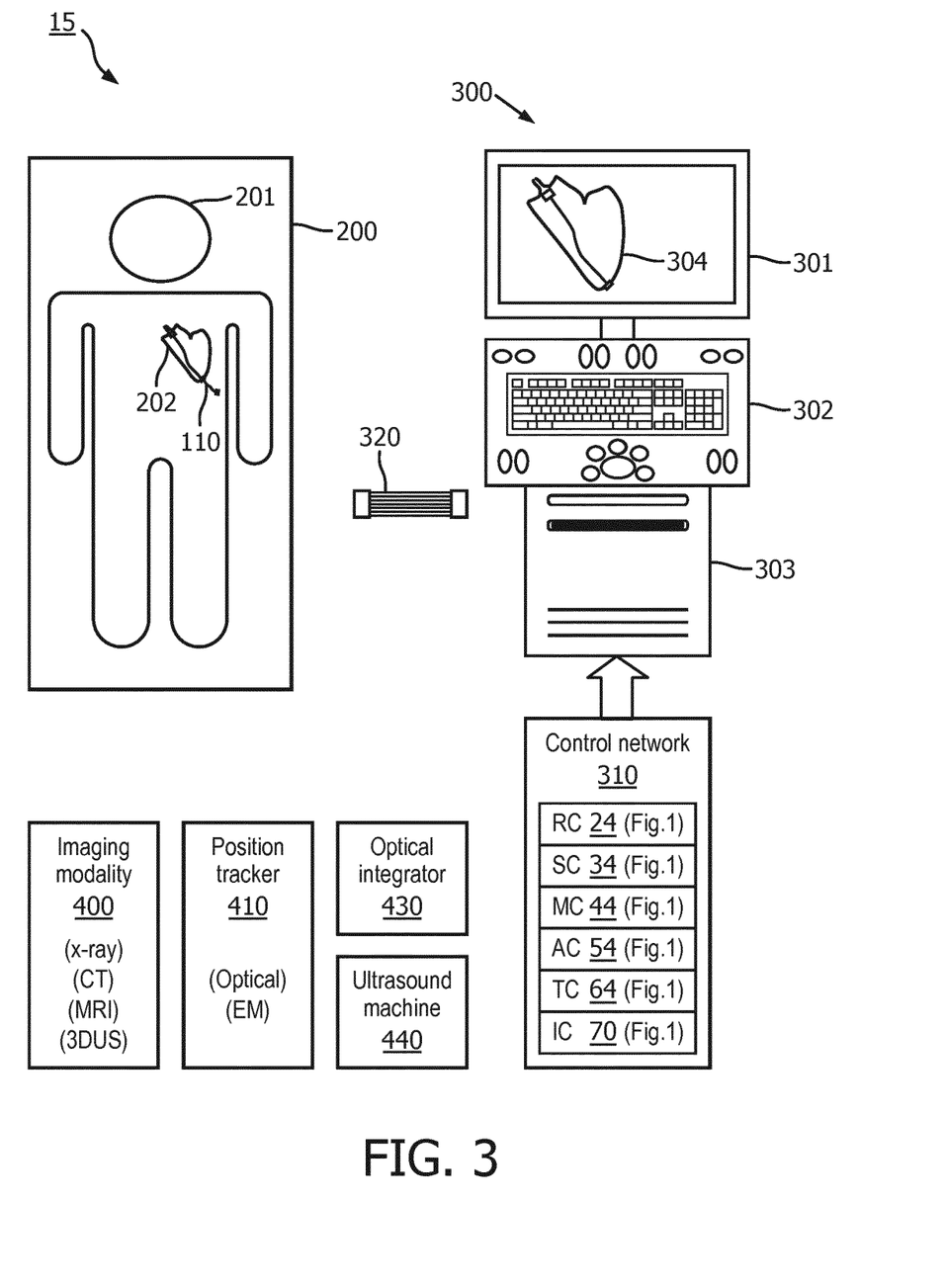
FIG. 3 illustrates an exemplary embodiment of an intervention system employing the multi-stage robot of FIG. 2 in accordance with the inventive principles of the present disclosure.
Figure 4:
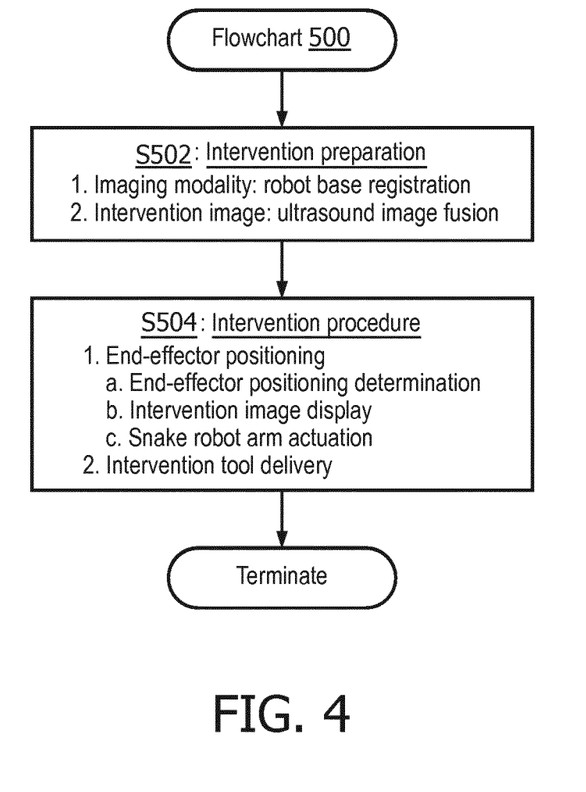
FIG. 4 illustrates a flowchart representative of an exemplary embodiment of an intervention method executable by the control network of FIG. 1 in accordance with the inventive principles of the present disclosure.

To facilitate a further understanding of the inventions of the present disclosure, the following description of FIGS. 3 and 4 teaches basic inventive principles of exemplary embodiments of an intervention system and an intervention method incorporating a multi-stage robot and a control network of the present disclosure. From this description, those having ordinary skill in the art will appreciate how to apply the inventive principles of the present disclosure to making and using numerous and varied embodiments of an intervention system and an intervention method incorporating a multi-stage robot and a control network of the present disclosure.

Referring to FIG. 3, an intervention system 15 is provided to perform an interventional procedure on a heart 202 of a patient 201 resting on an operating table 200. To this end, intervention system 15 incorporates multi-stage robot 110 as previously presented in the description of FIG. 2. Intervention system 15 further incorporates a control network 310 including registration controller 24, shape controller 34, motion controller 44, actuation controller 54, tracking controller 64 and intervention controller 74 as previously presented in the description of FIG. 1.

In practice, control network 310 may be distributed throughout intervention system 15.

In one embodiment, control network 310 is operated by a workstation 300 including an arrangement of a monitor 301, a keyboard 302 and a computer 303 as known in the art of the present disclosure.

As installed on computer 303, control network 310 includes processor(s), memory, a user interface, a network interface, and a storage interconnected via one or more system buses.

Each processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface.

The network interface may include one or more devices, as known in the art of the present disclosure or hereinafter conceived, for enabling communication with other hardware devices. In an non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent\

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage stores one or more application modules in the form of executable software/firmware for implementing the various functions of control network 310 as previously presented in the description of FIG. 1.

In practice, the controllers of control network 310 may be partially or wholly integrated within computer 303.

Still referring to FIG. 3, in a second embodiment, a controller of control network 310 may be installed on a different workstation/machine of intervention system 15.

For example, intervention system 15 may include an imaging modality 400 for generating preoperative and/or intraoperative intervention images of heart 202, and intervention controller 70 may be partially or fully installed within a workstation of imaging modality 400 for controlling an operation of imaging modality 400. Examples of imaging modality 400 include, but are not limited to, a stand-alone x-ray imaging system, a mobile x-ray imaging system, an ultrasound imaging system (e.g., TEE, TTE, IVUS, ICE), computed tomography ("CT") imaging system, positron emission tomography ("PET") imaging system, and magnetic resonance imaging ("MRI") system.

By further example, intervention system 15 may include a position tracker 410 for identifying the markers of the robot base 120 of robot 110 and imaging modality 400, and registration controller 24 may be partially or fully installed within a workstation of position tracker 410 for controlling an operation of position tracker 410.

By further example, intervention system 15 may include an optical integrator 430 for sensing a shape of the flexible robot arm 130 of robot 110, and shape controller 34 may be partially or fully installed within a workstation of optical integrator 430 for controlling an operation of optical integrator 430.

By further example, intervention system 15 may include an ultrasound apparatus 440 for energizing any ultrasound sensors of the end-effector of robot 110, and tracking controller 64 may be partially or fully installed a workstation of ultrasound apparatus 440 for controlling an operation of ultrasound apparatus 440.

Still referring to FIG. 3, via a connection to the robot base of robot 110, a cable connector 320 may be utilized to connect the sensors, actuators and/or encoders of robot 110 to computer 303, imaging modality 400, position tracker 410, optical integrator 430 and ultrasound apparatus 440 as needed.

FIG. 4 illustrates a flowchart 500 representative of an intervention method executed by control network 310 (FIG.) for implementing the interventional procedure.

Referring to FIGS. 3 and 4, a stage S502 of flowchart 500 is directed to preparation acts by control network 310 necessary for implementing the interventional procedure.

In one embodiment of S502, registration controller 24 as commanded by intervention controller 70 or via an operator of position tracker 410 controls an execution of a registration of imaging modality 400 and robot base 120 of multi-stage robot 110. For example, registration controller 24 operates position tracker 410 to identify a position of marker(s) affixed to imaging modality 400 and robot base 120 of robot 110 whereby registration controller 24 or intervention controller 70 execute a registration technique as known in the art of the present disclosure.

Additionally, if end-effector 160 of robot 110 includes ultrasound capability, tracking controller 74 as commanded by intervention controller 70 or via an operator of ultrasound machine 440 controls an execution of an ultrasound imaging of the left ventricle chamber of heart 202. For example, tracking controller 74 operates ultrasound machine 440 to energize the ultrasound transducers of end-effector 160 of robot 110 whereby tracking controller 74 or intervention controller 70 execute a generation of ultrasound images of the left ventricle chamber of heart 202 as known in the art of the present disclosure and to further execute an image based registration of an interventional images of the left ventricle chamber of heart 202 generated by imaging modality 400 and the ultrasound images of the left ventricle chamber of heart 202 generating by the ultrasound transducers of end-effector 160.

Still referring to FIGS. 3 and 4, a stage S504 of flowchart 500 is directed to interoperative acts by control network 310 necessary for implementing the interventional procedure.

In one embodiment of stage S504, intervention controller 70 processes data received from all of the sensors and encoders of robot 110 to determine an initial position of end-effector 160 of robot 110 within the left ventricle chamber of heart 202. More particularly, a position of end-effector 160 within the left ventricle chamber LV of the heart may be derived from (1) a registration of robot base 120 to a corresponding imaging modality, (2) a sensed shape of flexible robot arm 130, (3) a sensed physiological motion of the left ventricle chamber LV (if applicable), (4) a pose of each linkage of snake robot arm 150 relative to robot platform 140, and (5) an ultrasound imaging of the interior of the left ventricle chamber LV (if applicable).

From the initial position determination of end-effector 160 of robot 110, intervention controller 70 controls a display of an intervention image 304 of the left ventricle chamber of heart 202. In practice, intervention image 304 may be a preoperative or an intraoperative image whereby an overlay of robot 110 may be provided on image 304 based on a position of end-effector 160 of robot 110 within the left ventricle chamber of heart 202 determined by intervention controller 70. Alternatively, intervention image 304 may be an intraoperative image whereby intervention controller 70 provides an indication of a position of end-effector 160 of robot 110 within the left ventricle chamber of heart 202 determined by intervention controller 70. Concurrently, an ultrasound image generated from any ultrasound transducers of end-effector 160 may be fused with intervention image 304 of the left ventricle chamber of heart 202.

At this point, there are two (2) general modes of snake robot arm actuation.

The first mode involves intervention controller 70 controlling an actuation of snake robot arm 150 of robot 110 to position end-effector 160 at or relative to a target position for an intervention tool within the left ventricle chamber of heart 202 in accordance with a preoperative plan as known in the art of the present disclosure.

The second mode involves an operator of workstation 300 manually actuating snake robot arm 150 of robot 110 to position end-effector 160 at or relative to a target position for an intervention tool within the left ventricle chamber of heart 202 in accordance with a preoperative plan as known in the art of the present disclosure.

For either mode, intervention controller 70 facilitates any adjustments to the preoperative plan via intervention controller 70 or the operator as necessary for end-effector 160 at or relative to an original target position or new target position for an intervention tool within the left ventricle chamber of heart 202.

Upon end-effector 160 reaching the target position, the aortic valve replacement is delivered for treatment of the aortic valve as known in the art of the present disclosure.

While FIGS. 3 and 4 were described in terms of an aortic valve replacement by a robot 110 (FIG. 2), those having ordinary skill in the art will appreciate how to apply the inventive principles of the present disclosure to robot 110 and additional embodiments of a multi-stage robot of the present disclosure for implementing an aortic valve replacement or any other type of interventional procedure for an anatomical structure.

Referring to FIGS. 1-4, those having ordinary skill in the art of the present disclosure will appreciate numerous benefits of the inventions of the present disclosure including, but not limited to, a multi-stage robot facilitating an accurate registration of an end-effector within an anatomical structure that improves upon an efficient of imaging, diagnostic and/or treatment delivery of an intervention tool to the anatomical structure.

Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed.

Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive multi-stage robots (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A multi-stage robot for delivery of an intervention tool within an anatomical structure, the multi-stage robot comprising:
   a sequential series arrangement of a flexible robot arm, a robot platform, a snake robot arm, and an end-effector, wherein (i) a proximal end of the robot platform is attached to a distal end of the flexible robot arm and (ii) a distal end of the robot platform is attached to a proximal end of the snake robot arm,
   wherein the flexible robot arm, the robot platform, the snake robot arm, and the end-effector are structured to be introduced through a first incision or a first anatomical opening into an anatomical region enclosing the anatomical structure,
   wherein the snake robot arm and the end-effector are further structured to be introduced through a second incision or a second anatomical opening into the anatomical structure,
   wherein the robot platform comprises a structure configured to attach to the second incision or the second anatomical opening into the anatomical structure and position the flexible robot arm within the anatomical region and the snake robot arm within the anatomical structure, and
   wherein the snake robot arm is actuatable relative to the robot platform to target position the end-effector within the anatomical structure.

2. The multi-stage robot of claim 1, wherein the sequential series arrangement of the flexible robot arm, the robot platform, the snake robot arm, and the end-effector define a channel extending from the flexible robot arm through the robot platform to the snake robot arm.

3. The multi-stage robot of claim 1, wherein the sequential series arrangement of the flexible robot arm, the robot platform, the snake robot arm, and the end-effector define a channel extending from the flexible robot arm through the robot platform and the snake robot arm to the end-effector.

4. The multi-stage robot of claim 1, wherein the flexible robot arm includes at least one shape sensor operable for sensing a shape of the flexible robot arm.

5. The multi-stage robot of claim 1, wherein the robot platform includes at least one motion tracking sensor operable for sensing a motion of the robot platform.

6. The multi-stage robot of claim 1, wherein the end-effector includes at least one ultrasound imaging device operable for imaging an interior of the anatomical structure.

7. The multi-stage robot of claim 1, wherein the sequential series arrangement includes a robot base, the flexible robot arm, the robot platform, the snake robot arm, and the end-effector.

8. The multi-stage robot of claim 7,
wherein the robot base is structured to be attachable to the first incision or the first anatomical opening into the anatomical region.

9. The multi-stage robot of claim 7,
wherein the robot base includes at least one marker operable for identifying a position of the robot base within an intervention space.

10. The multi-stage robot of claim 7,
wherein the sequential series arrangement of the robot base, the flexible robot arm, the robot platform, the snake robot arm, and the end-effector define a channel extending from the robot base through the flexible robot arm and the robot platform to the snake robot arm.

11. The multi-stage robot of claim 7,
wherein the sequential series arrangement of the flexible robot arm, the robot platform, the snake robot arm, and the end-effector define a channel extending from the robot base through the flexible robot arm, the robot platform and the snake robot arm to the end-effector.

12. The multi-stage robot of claim 1, wherein the structure of the robot platform configured to attach to the second incision or the second anatomical opening comprises at least one of a cuff or a clip configured to attach to the second incision or the second anatomical opening.

13. An intervention method for delivery of an intervention tool within an anatomical structure, the intervention method comprising:
introducing a multi-stage robot including a flexible robot arm, a robot platform, a snake robot arm, and an end-effector through a first incision or a first anatomical opening into an anatomical region enclosing the anatomical structure, wherein (i) a proximal end of the robot platform is attached to a distal end of the flexible robot arm and (ii) a distal end of the robot platform is attached to a proximal end of the snake robot arm;
introducing the snake robot arm and the end-effector through a second incision or a second anatomical opening into the anatomical structure;
attaching the robot platform to the second incision or the second anatomical opening of the anatomical structure, such that the robot platform positions the flexible robot arm within the anatomical region and positions the snake robot arm within the anatomical structure; and
actuating the snake robot arm within the anatomical structure relative to the robot platform to target position the end-effector within the anatomical structure.

14. The intervention method of claim 13, further comprising:
determining a position of the end-effector within the anatomical structure relative to the robot platform based on at least one of:
a registration of a robot base of the multi-stage robot to an imaging modality,
a sensed shape of the flexible robot arm, and
a pose of the actuated snake robot arm relative to the robot platform.

15. The intervention method of claim 14, further comprising:
determining a position of the end-effector within the anatomical structure based on at least one of:
a physiological motion of the anatomical structure as sensed by the robot platform, and
an ultrasound image of an interior of the anatomical structure generated by the end-effector.

16. The intervention method of claim 13, further comprising:
attaching a robot base of the multi-stage robot to the first incision or the first anatomical opening into the anatomical region.

17. The intervention method of claim 13, further comprising:
introducing the interventional tool through the multi-stage robot into the anatomical structure.

18. The intervention method of claim 13, wherein a structure of the robot platform is configured to attach to the second incision or the second anatomical opening and comprises at least one of a cuff or a clip configured to attach to the second incision or the second anatomical opening.

* * * * *